US012773473B2

(12) United States Patent
Zheng

(10) Patent No.: US 12,773,473 B2
(45) Date of Patent: Oct. 27, 2026

(54) NANOPARTICLE-COATED COLLAGEN IMPLANT

(71) Applicant: Orthocell Limited, Murdoch (AU)

(72) Inventor: Ming-Hao Zheng, City Beach (AU)

(73) Assignee: Orthocell Limited, W.A. (AU)

( * ) Notice: Subject to any disclaimer, the term of this patent is extended or adjusted under 35 U.S.C. 154(b) by 1377 days.

(21) Appl. No.: 17/275,602

(22) PCT Filed: Sep. 13, 2019

(86) PCT No.: PCT/AU2019/050985

§ 371 (c)(1),
(2) Date: Mar. 11, 2021

(87) PCT Pub. No.: WO2020/051647

PCT Pub. Date: Mar. 19, 2020

(65) Prior Publication Data

US 2021/0322634 A1 Oct. 21, 2021

(30) Foreign Application Priority Data

Sep. 14, 2018 (AU) ................................ 2018903475

(51) Int. Cl.

| | |
|---|---|
| ***A61L 27/24*** | (2006.01) |
| ***A61L 27/04*** | (2006.01) |
| ***A61L 27/36*** | (2006.01) |
| ***A61L 27/58*** | (2006.01) |
| ***B82Y 5/00*** | (2011.01) |
| ***B82Y 30/00*** | (2011.01) |

(52) U.S. Cl.

CPC ............... *A61L 27/24* (2013.01); *A61L 27/04* (2013.01); *A61L 27/365* (2013.01); *A61L 27/58* (2013.01); *B82Y 5/00* (2013.01); *B82Y 30/00* (2013.01); *A61L 2300/104* (2013.01); *A61L 2300/406* (2013.01); *A61L 2300/41* (2013.01); *A61L 2400/18* (2013.01); *A61L 2420/02* (2013.01); *A61L 2420/08* (2013.01); *A61L 2430/02* (2013.01); *A61L 2430/12* (2013.01); *A61L 2430/24* (2013.01)

(58) Field of Classification Search

CPC ........ A61L 27/24; A61L 27/04; A61L 27/365; A61L 27/58; A61L 2300/104; A61L 2300/406; A61L 2300/41; A61L 2400/18; A61L 2420/02; A61L 2420/08; A61L 2430/02; A61L 2430/12; A61L 2430/24; A61L 27/306; A61L 27/54; A61L 2300/404; A61L 2400/12; A61L 27/446; A61L 27/56; A61L 2202/21; A61L 2300/606; A61L 2420/04; A61L 2420/06; A61L 2430/40; B82Y 5/00; B82Y 30/00; A61F 2/32; A61F 2/38; A61F 2/40; A61F 2002/30751; A61F 2310/00371; A61F 2310/0052; A61F 2/0095; A61F 2250/0081; A61F 2310/00401; A61F 2310/00413; A61F 2310/00461; A61F 2310/00467; A61F 2310/00568; A61C 8/0012; A61C 8/0013; A61C 8/005; B01J 19/10; B01J 2219/00486

See application file for complete search history.

(56) References Cited

U.S. PATENT DOCUMENTS

| | | | | |
|---|---|---|---|---|
| 9,096,688 | B2 | 8/2015 | Zheng | |
| 2008/0044657 | A1* | 2/2008 | Woo .................. | A61K 49/0052 428/407 |
| 2010/0255447 | A1* | 10/2010 | Biris .................... | A61L 27/306 523/105 |
| 2013/0029030 | A1* | 1/2013 | Larsen ................ | A61L 24/0036 427/2.31 |
| 2014/0287018 | A1 | 9/2014 | Soo et al. | |
| 2020/0023014 | A1 | 1/2020 | Morales | |

FOREIGN PATENT DOCUMENTS

| | | | | |
|---|---|---|---|---|
| CN | 105327398 | | 2/2016 | |
| EP | 1991365 | | 12/2014 | |
| JP | 0621044 | A2 * | 4/1994 | ............ A61L 27/00 |
| JP | H6-304241 | | 11/1994 | |
| WO | WO2006026026 | | 3/2006 | |
| WO | WO2007032001 | | 3/2007 | |
| WO | WO-2007032001 | A2 * | 3/2007 | ............ C23C 18/02 |

(Continued)

OTHER PUBLICATIONS

Behring et al., (2008) "Toward guided tissue and bone regeneration: morphology, attachment, proliferation, and migration of cells cultured on collagen barrier membranes. A systematic review", Odontology, 96:1-11.

Chuangang et al., (2017) "Silver nanoparticle loaded collagen/chitosan scaffolds promote wound healing via regulating fibroblast migration and macrophage activation.", Scientific Reports, 7(10489):1-11.

Ding et al., (2011) "Rapid repair of rat sciatic nerve injury using a nanosilver-embedded collagen scaffold coated with laminin and fibronectin.", Regenerative medicine, 6(4):437-447.

Donos et al., (2002) "Alveolar ridge augmentation by combining autogenous mandibular bone grafts and non-resorbable membranes An experimental study in the rat", Clin. Oral Impl. Res., 185-191.

Donos et al., (2002) "Alveolar ridge augmentation using a resorbable copolymer membrane and autogenous bone grafts an experimental study in the rat", Clin. Oral Impl. Res., 203-313.

(Continued)

*Primary Examiner* — Snigdha Maewall

(74) *Attorney, Agent, or Firm* — Rudy J. Ng; Bozicevic, Field & Francis LLP

(57) ABSTRACT

The invention relates to a method of producing an implantable collagen-containing medical device comprising the step of coating said collagen-containing medical device with metal microparticles and/or metal nanoparticles, wherein said step of coating said collagen-containing medical device is by sonication such that the collagen-containing medical device has anti-bacterial and anti-inflammatory properties on implantation compared to the medical device not coated with metal microparticles and/or metal nanoparticles.

17 Claims, 9 Drawing Sheets

Specification includes a Sequence Listing.

(56) References Cited

FOREIGN PATENT DOCUMENTS

| | | | |
|---|---|---|---|
| WO | WO2013/167417 | 11/2013 | |
| WO | WO-2017125388 A1 * | 7/2017 | ............ C08K 5/092 |

OTHER PUBLICATIONS

Gaidau et al., (2009) "Investigations on antimicrobial activity of collagen and keratin based materials doped with silver nanoparticles.", Biotechnology Letters, 14(5):4665-4672.

Jensen and Terheyden, (2009) "Bone Augmentation Procedures in Localized Defects in the Alveolar Ridge: Clinical Results with Different Bone Grafts and Bone-Substitute Materials", Supplement, 24:218-236.

Kesting et al., (2008) "Severe Osteomyelitis Following Immediate Placement of a Dental Implant", Int J Oral Maxillofac Implants, 23:137-142.

McLaughlin et al., (2016) "Sprayable peptide-modified silver nanoparticles as a barrier against bacterial colonization.", Nanoscale, 8(46):19200-19203.

Mucha et al., (2012) "Novel technique of polymer composite preparation for bone implants." Advanced Materials Research, 488-489:681-685.

Roccuzzo et al., (2007) "Autogenous bone graft alone or associated with titanium mesh for vertical alveolar ridge augmentation: a controlled clinical trial", Clin. Oral Impl. Res., 286-294.

Shnaiderman-Shapiro et al., (2015) "Histopathological Spectrum of Bone Lesions Associated with Dental Implant Failure: Osteomyelitis and Beyond", Head and Neck Pathol, 9:140-146.

You et al., (2017) "Silver nanoparticle loaded collagen/chitosan scaffolds promote wound healing via regulating fibroblast migration and macrophage activation", Scientific Reports, 7(10489):1-11.

Zitzmann et al., (2001) "Alveolar Ridge Augmentation with Bio-Oss: A Histologic Study in Humans", The International Journal of Periodontics & Restorative Dentistry, 21(3):1-7.

Behring, Jan, et al., (2008) "Toward guided tissue and bone regeneration: morphology, attachment, proliferation, and migration of cells cultured on collagen barrier membranes. A systematic review", Odontology, 96:1-11.

Ding, Tan, et al., (2011) "Rapid repair of rat sciatic nerve injury using a nanosilver-embedded collagen scaffold coated with laminin and fibronectin", Regen. Med., 6(4):437-447.

Donos, Nikolaus, et al., (2002a) "Alveolar ridge augmentation using a resorbable copolymer membrane and autogenous bone grafts an experimental study in the rat", Clin. Oral Impl. Res., 13:203-213.

Donos, Nikolaus, et al., (2002b) "Alveolar ridge augmentation using a resorbable copolymer membrane and autogenous bone grafts an experimental study in the rat", Clin. Oral Impl. Res., 13:185-191.

Gaidau, Carmen, et al., (2009) "Investigations on Antimicrobial Activity of Collagen and Keratin Based Materials doped with Silver Nanoparticles", Romanian Biotechnological Letters, 14(5):4665-4672.

Jensen, Simon Storgard and Terheyden, Hendrik, (2009) "Bone Augmentation Procedures in Localized Defects in the Alveolar Ridge: Clinical Results with Different Bone Grafts and Bone-Substitute Materials", The International Journal of Oral & Maxillofacial Implants, 24(Supplement):218-236.

Kesting, Marco, Rainer, et al., (2008) "Severe Osteomyelitis Following Immediate Placement of a Dental Implant", Int J Oral Maxillofac Implants, 23(1):137-142.

McLaughlin, Sarah, et al., (2016) "Sprayable peptide-modified silver nanoparticles asa barrier against bacterial colonization", Nanoscale, 8:19200-19203.

Mucha, Maria and Tylman, Michal, (2012) "Novel technique of polymer composite preparation for bone implants", Advanced Materials Research, 488-489:681-685.

Roccuzzo, Mario, et al., (2006) "Autogenous bone graft alone or associated with titanium mesh for vertical alveolar ridge augmentation: a controlled clinical trial", Clin. Oral Impl. Res., 18:286-294.

Shnaiderman-Shapiro, Anna, et al., (2015) "Histopathological Spectrum of Bone Lesions Associated with Dental Implant Failure: Osteomyelitis and Beyond", Head and Neck Pathol, 9:140-146.

You, Chuangang, et al., (2017) "Silver nanoparticle loaded collagen/chitosan scaffolds promote wound healing via regulating fibroblast migration and macrophage activation", Scientific Reports, 7(10489):1-11.

Zitzmann, Nicola, U., et al., (2001) "Alveolar Ridge Augmentation with Bio-Oss: A Histologic Study in Humans", The International Journal of Periodontics & Restorative Dentistry, 21(3):1-7.

Cardoso et al, (2004) "Collagen-based silver nanoparticles for biological applications: synthesis and characterization", Journal of Biotechnology, vol. 12, No. 36, pp. 1/1-9/9.

* cited by examiner

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1

gccgggaatg atgagaacta                                           20


<210> SEQ ID NO 2
<211> LENGTH: 20
<212> TYPE: DNA
<213> ORGANISM: Artificial Sequence
<220> FEATURE:
<223> OTHER INFORMATION: synthetic primer

<400> SEQUENCE: 2

ggaccgtcca ctgtcacttt                                           20


<210> SEQ ID NO 3
<211> LENGTH: 21
<212> TYPE: DNA
<213> ORGANISM: Artificial Sequence
<220> FEATURE:
<223> OTHER INFORMATION: synthetic primer

<400> SEQUENCE: 3

gaagctctgg gtgcaggata g                                         21


<210> SEQ ID NO 4
<211> LENGTH: 21
<212> TYPE: DNA
<213> ORGANISM: Artificial Sequence
<220> FEATURE:
<223> OTHER INFORMATION: synthetic primer

<400> SEQUENCE: 4

tgtgtttccc aggagagaat g                                         21


<210> SEQ ID NO 5
<211> LENGTH: 20
<212> TYPE: DNA
<213> ORGANISM: Artificial Sequence
<220> FEATURE:
<223> OTHER INFORMATION: synthetic primer
```

<400> SEQUENCE: 5
cccggtgaaa gtgactgatt 20

<210> SEQ ID NO 6
<211> LENGTH: 22
<212> TYPE: DNA
<213> ORGANISM: Artificial Sequence
<220> FEATURE:
<223> OTHER INFORMATION: synthetic primer

<400> SEQUENCE: 6
ttcttcagag gacacagcat tc 22

<210> SEQ ID NO 7
<211> LENGTH: 23
<212> TYPE: DNA
<213> ORGANISM: Artificial Sequence
<220> FEATURE:
<223> OTHER INFORMATION: synthetic primer

<400> SEQUENCE: 7
ccctcacact cagatcatct tct 23

<210> SEQ ID NO 8
<211> LENGTH: 19
<212> TYPE: DNA
<213> ORGANISM: Artificial Sequence
<220> FEATURE:
<223> OTHER INFORMATION: synthetic primer

<400> SEQUENCE: 8
gctacgacgt gggctacag 19

<210> SEQ ID NO 9
<211> LENGTH: 21
<212> TYPE: DNA
<213> ORGANISM: Artificial Sequence
<220> FEATURE:
<223> OTHER INFORMATION: synthetic primer

<400> SEQUENCE: 9
ctgcaagaga cttccatcca g 21

<210> SEQ ID NO 10
<211> LENGTH: 23
<212> TYPE: DNA
<213> ORGANISM: Artificial Sequence
<220> FEATURE:
<223> OTHER INFORMATION: synthetic primer

<400> SEQUENCE: 10
agtggtatag acaggtctgt tgg 23

<210> SEQ ID NO 11
<211> LENGTH: 20
<212> TYPE: DNA
<213> ORGANISM: Artificial Sequence
<220> FEATURE:
<223> OTHER INFORMATION: synthetic primer

<400> SEQUENCE: 11
cttcccactt gctgaaaagg 20

<210> SEQ ID NO 12
<211> LENGTH: 20

-continued

```
<212> TYPE: DNA
<213> ORGANISM: Artificial Sequence
<220> FEATURE:
<223> OTHER INFORMATION: synthetic primer

<400> SEQUENCE: 12

cgaagagacc gaatcccata                                                20
```

NANOPARTICLE-COATED COLLAGEN IMPLANT

FIELD

The present invention relates to a metal nanoparticle-coated collagen material which has anti-bacterial and anti-inflammatory properties. The invention also relates to methods of fabrication.

BACKGROUND

Annually, millions of implants are placed inside of organisms, including humans and animals. Most of these implants serve complex roles including but not limited to tissue replacement, mechanical support, tissue generation, cosmetic enhancement, complete or partial limb replacement, joint replacement, tooth replacement, spine reconstruction, defibrillators/pacemakers, in addition to electrodes and wires.

Most implants are made of metals, metal oxides, polymeric materials or tissue components obtained from animals or humans. Consequently, implant bio-compatibility poses a limitation in many applications as implants need to perform complex functions in the human body and their binding to the host tissue is crucial. For example, dental implants need to adhere very strongly to the jaw bone. It is also important for implant surfaces to prevent or reduce biofilm formation, which leads to infection and implant failure. Likewise, implants used for hip or knee replacements must integrate very closely and strongly with the bone structure of the skeleton. To meet these requirements, implants are constructed from bio-compatible materials such as titanium, polymeric materials, or ceramic materials. Still a relatively large number of such materials are being rejected every year by human patients and in most of these cases, the reasons are related to the poor integration of the implant surface with the bone/tissue structure and the growth and adherence of cells at the implant surface. Furthermore, many implants are lost due to infections caused by growth of biofilm on the implant surface.

Dental implant is an effective and common treatment for managing missing teeth in edentulous patients (Pye et al., Journal of Hospital infection, 2009, 72(2): p. 104-110). The success of dental implants relies on the solid anchorage and integration between implant and alveolar bone, thus maintaining adequate bone volume in alveolar bone is important (Semb, Alveolar bone grafting in Cleft Lip and Palate. 2012, Karger Publishers. p. 124-136; Simon et al., Journal of Periodontology, 2000. 71(11): p. 1774-1791). However, as exodontia and trauma can often lead to degradation in alveolar ridge, and subsequent infection and inflammation can further accelerate this progress (Allegrini et al. Alveolar ridge sockets preservation with bone grafting—review. in Annales Academiae Medicae Stetinensis. 2008; Cordaro et al., Clinical oral implants research, 2002. 13(1): p. 103-111), alveolar ridge reconstruction is often required before tooth implantation (Jensen & Terheyden, International Journal of Oral & Maxillofacial Implants, 2009. 24; Roccuzzo et al., Clinical oral implants research, 2007. 18(3): p. 286-294). Traditionally, the procedure is to infill bone substitute into alveolar socket to initiate bone formation (Zitzmann et al., International Journal of Periodontics & Restorative Dentistry, 2001. 21(3)). Even though bone substitute has been well developed, fast-growing connective tissue, like gingiva, can infiltrate inside of graft packet and impair new-bone formation (Donos et al., Clinical Oral Implants Research, 2002. 13(2): p. 203-213; Donos et al., Clinical Oral Implants Research, 2002. 13(2): p. 185-191). In addition, the local microenvironment of the original teeth conditions is often susceptible to infection which can increase the incidence of graft debridement and even osteomyelitis (Kesting et al. International Journal of Oral & Maxillofacial Implants, 2008. 23(1); Shnaiderman-Shapiro et al., Head and neck pathology, 2015. 9(1): p. 140-146). Therefore, a barrier of anti-bacterial and anti-inflammatory material with the ability to guide bone regeneration and prevent soft tissue ingrowth in dental implant is in high demand.

Collagen, a natural material with excellent biocompatibility, has been widely used in clinical applications (Shen et al., Acta biomaterialia, 2008. 4(3): p. 477-489; Donzelli et al., Archives of oral biology, 2007. 52(1): p. 64-73; Lee et al., Journal of Orthopaedic Research, 2003. 21(2): p. 272-281). Collagen biomaterials have been shown to promote and regulate tissue regeneration (Ma et al., Biomaterials, 2003. 24(26): p. 4833-4841; Ferreira et al., Acta biomaterialia, 2012. 8(9): p. 3191-3200; Prescott et al., Journal of endodontics, 2008. 34(4): p. 421-426). Specifically, in bone tissue, collagen scaffolds have demonstrated the capacity for guided-bone regeneration (GBR) (Behring et al., Odontology, 2008. 96(1): p. 1-11). Despite the excellent GBR properties of collagen, most collagen implants do not possess local anti-bacterial and anti-inflammatory effects.

Thus, there is a continuing need to develop implants that have superior properties of attachment, cellular growth promotion, while being resistant to infections caused by growth of biofilm on the implant surface.

SUMMARY

Embodiments herein include but are not limited to methods, devices, compositions, kits, materials, tools, instruments, reagents, products, compounds, pharmaceuticals, arrays, computer-implemented algorithms, and computer-implemented methods.

In one aspect, there is provided a method of producing an implantable collagen-containing medical device comprising the step of coating said collagen-containing medical device with metal microparticles and/or metal nanoparticles, wherein said step of coating said collagen-containing medical device is by sonication such that the collagen-containing medical device has anti-bacterial and anti-inflammatory properties on implantation compared to the medical device not coated with metal microparticles and/or metal nanoparticles.

In one embodiment, the medical device can be delivered into a host organism, such as a human or animal, or used in vitro. The medical device may comprise plasmids, genes, nucleic acids, or a DNA or RNA virus.

In another embodiment, the coating covers at least a portion of said device. The metal micro and/or nanoparticle coating can further comprise natural or synthetic polymers, metal, metal oxide, oxide, metal nitride, borate, ceramic, zirconia, allograft hard tissue, allograft soft tissue, xenograft hard tissue, xenograft soft tissue, carbon nanostructure, carbon, glasses, natural, or biocompatible material. The coating is capable of performing at least one of treating infection, preventing infection; promoting cell adhesion; preventing biofilm formation, inhibiting biofilm formation; promoting cell proliferation; promoting binding with a biological or non-biological system, increasing or decreasing a cell function; delivering a drug and/or bioactive agent, or ensuring a better integration of a material into the host tissue.

In other embodiments, the coating comprises one or more layers of nanoparticles and/or microparticles. In still other embodiments, the one or more layers comprises a single type of nanoparticle and/or microparticle, or a combination of more than one type of nanoparticle and/or microparticle. Further, one or more layers comprises silver nanoparticles. In another embodiment, one or more layers comprises a combination of metal, nanoparticles, metal oxides, carbon nanotubes, polymeric nanoparticles, ceramics, calcium phosphate, collagen, and/or hydroxyapatite nanoparticles. In other embodiments, the coating is biodegradable and/or biocompatible, and nanoparticles can be released from said nanoparticle composition as each layer degrades. In other embodiments, a drug, growth factor, and/or bioactive agent is deposited within at least one layer and/or on the surface layer of said coating. In other embodiments, the nanoparticles comprise gold, silver, metals, oxides, carbon nanostructures (single, double, multi walled nanotubes, graphenes, fullerenes, nanofibers), hydroxyapatite, zirconia, natural or synthetic polymers, ceramics, or metal oxide.

In other embodiments, the medical device is an orthopaedic implant, dental implant, veterinary prosthetic device, tissue engineering matrix, allograft hard tissue or allograft soft tissue. The orthopaedic implant is a hip implant, knee implant, shoulder implant, plate, pin, screw, wire, or rod. The dental implant is an abutment, healing screw, or cover screw. The veterinary prosthetic device is an implant, pin, screw, plate, or rod.

In other embodiments, the coating comprises one or more layers comprise at least one of a protein, amino acid, enzyme, nucleic acid, bioactive agent, growth factor, drug, antibiotic, nucleic acid, hormone, antibody, or agent that inhibits biofilm formation and may be released as layer(s) degrade. In a further embodiment, the growth factor is a bone morphogenic protein capable of promoting bone formation adjacent to or on the surface of a device. In another embodiment, the bioactive agent is in or on the surface coating of a medical device and affects adjacent tissue or cells in at least one or more of bone formation, protein synthesis, gene, expression, cell proliferation, mitosis, DNA transcription, hormone production, enzyme production, cell death, gene delivery, or drug delivery. In a still further embodiment, the bioactive agent may be linked to said nanoparticles and the linkage may be a covalent, ionic, hydrogen bond, sulfide bond, or polar covalent bond.

In another aspect, there is provided a method for inhibiting biofilm formation on a collagen-containing medical implant, comprising the step of coating said medical implant with metal microparticles and/or nanoparticles by sonication such that the medical implant on implantation has anti-bacterial and anti-inflammatory properties compared to the medical implant not coated with metal microparticles and/or nanoparticles by sonication.

Also provided is a collagen-containing medical implant coated with metal microparticles and/or nanoparticles by sonication for use in a method for inhibiting biofilm formation on the medical implant, wherein the medical implant on implantation has anti-bacterial and anti-inflammatory properties compared to the medical implant not coated with metal microparticles and/or nanoparticles by sonication.

In one embodiment, a biofilm is a bacterial, fungal, or protozoan biofilm. In another embodiment, a medical implant is an orthopaedic or dental implant, graft, bone material, scaffold, allograft hard tissue, allograft soft tissue or tissue engineering matrix.

In another aspect, there is provided a method for inhibiting microbial colonization on a collagen-containing medical device or implant, comprising coating said device or implant with metal microparticles and/or metal nanoparticles by sonication that prevents microbial colonization.

Also provided is a collagen-containing medical device or implant coated with metal microparticles and/or nanoparticles by sonication for use in a method for inhibiting microbial colonization on the device or implant, wherein the metal microparticles and/or nanoparticles prevent microbial colonization.

In one embodiment, the collagen-containing device or implant is a dental implant, orthopaedic implant, veterinary implant, scaffold or tissue engineering matrix.

In another aspect, there is a collagen-containing implant comprising silver nanoparticles, wherein said silver nanoparticles coat at least one surface of said implant. In one embodiment, the implant is a dental implant or an abutment for a dental implant.

In another aspect, there is provided a method of sterilizing a collagen-containing metal nanoparticle-coated medical device, comprising exposing said device to either ethylene oxide or gamma radiation.

In another aspect, there is provided a package comprising a collagen-containing metal nanoparticle-coated medical device, wherein said device is sealed in an airtight or vacuum packed container. In one embodiment, the medical device is a dental implant, an abutment for a dental implant, or any medical device.

In another aspect, there is provided a method for enhancing bone cell growth, comprising (a) depositing metal nanoparticles on a surface of a collagen-containing membrane to create a surface coating; and (b) culturing osteoblasts on said surface.

DETAILED DESCRIPTION

Figure 1:
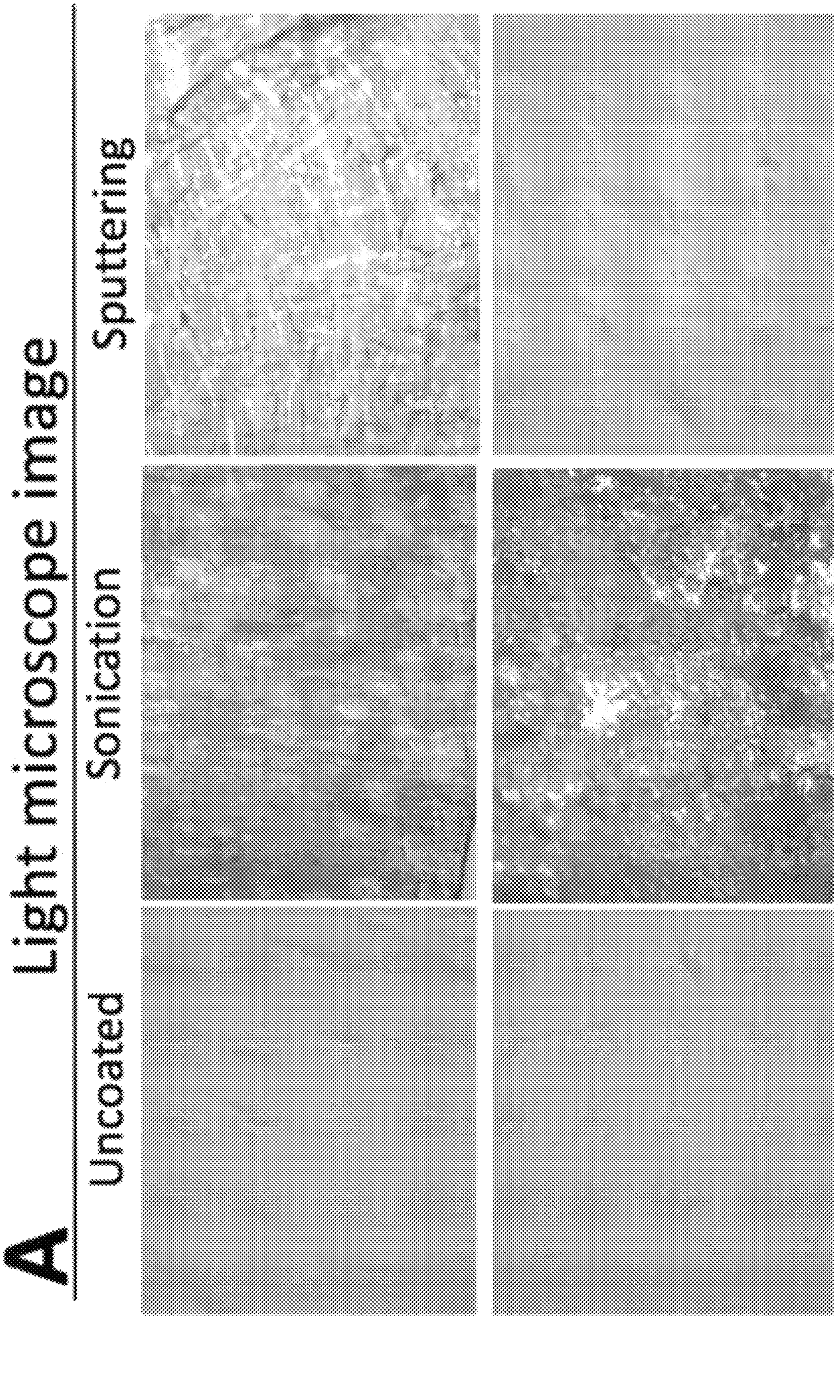
FIG. 1. Characterization of AgNP-coated collagen membrane. A Light microscopy image of both sides of uncoated and coated membranes. B Scanning electron microscopy (SEM) images of AgNP-coated collagen membrane using sonication at different concentrations of AgNP solution and using sputtering coating. C AgNP content (mg) on coated collagen membrane.
Figure 1:
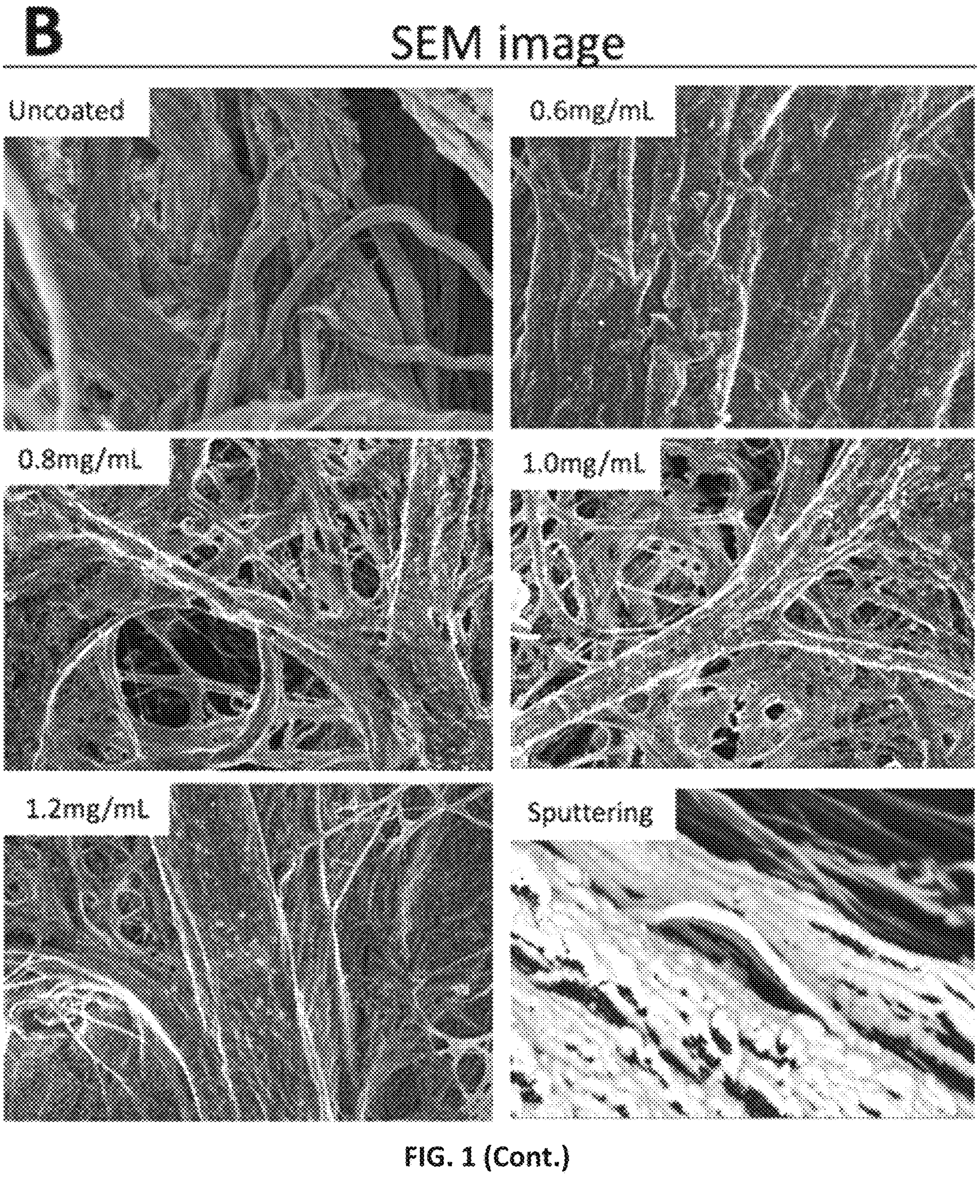
Figure 1:
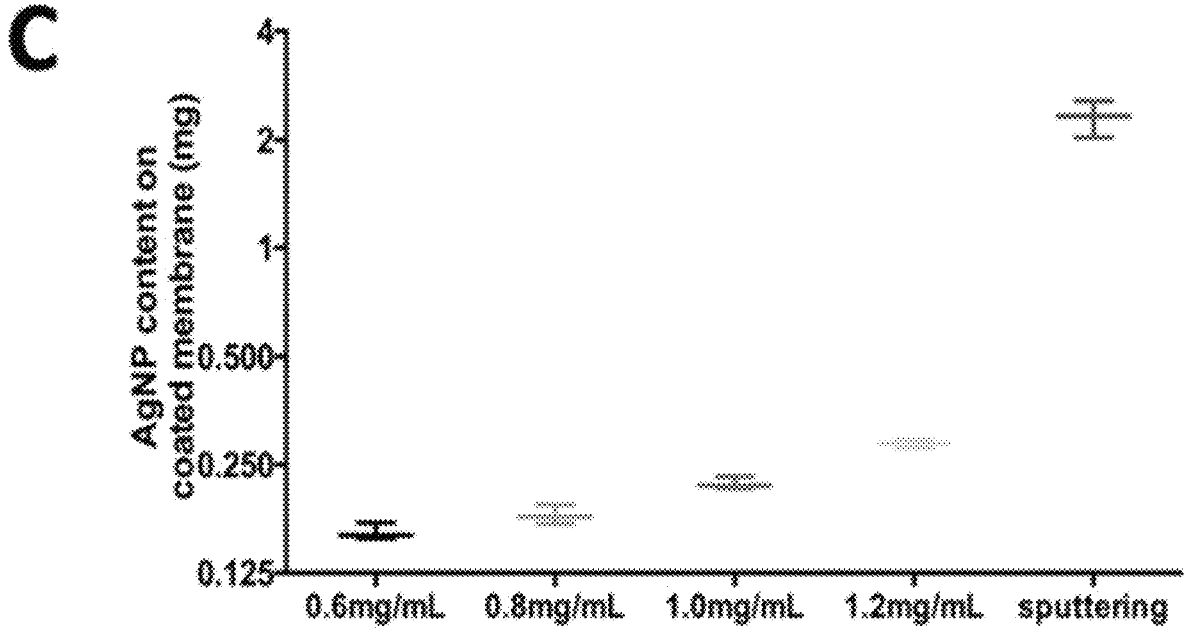

Methodologies, materials, and devices provided herein relate to a nanoparticle (NP) or microparticle metal coating that can be applied to the surface of a collagen-containing implant. More specifically, and as described below, a surface coating can be applied to any collagen-containing implant, such as a medical or dental implant, wherein the coating is bio-compatible, optionally bio-degradable, and facilitates surface adherence and proliferation of cells adjacent to and/or on an implant surface. The surface coating can also deliver drugs and/or bioactive agents that can lead to increased cell proliferation and bone mineralization at the implant surface. Surface coatings can also reduce and prevent growth of biofilm and aid in the treatment and/or prevention of inflammation.

All technical terms used herein are terms commonly used in cell biology, biochemistry, molecular biology, and nanotechnology and can be understood by one of ordinary skill in the art to which this invention belongs. These technical terms can be found in the current editions of Molecular Cloning: A Laboratory Manual, (Sambrook et al., Cold Spring Harbor); Gene Transfer Vectors for Mammalian Cells (Miller & Calos eds.); and Current Protocols in Molecular Biology (F. M. Ausubel et al. eds., Wiley & Sons). Cell biology, protein chemistry, and antibody techniques can be found in Current Protocols in Protein Science (J. E. Colligan et al. eds., Wiley & Sons); Current Protocols in Cell Biology (J. S. Bonifacino et al., Wiley & Sons) and Current Protocols in Immunology (J. E. Colligan et al. eds., Wiley & Sons.). Reagents, cloning vectors, and kits are available from commercial vendors such as BioRad, Stratagene, Invitrogen, ClonTech, and Sigma-Aldrich Co.

Cell culture methods are described generally in the current edition of Culture of Animal Cells: A Manual of Basic Technique (R. I. Freshney ed., Wiley & Sons); General Techniques of Cell Culture (M. A. Harrison & I. F. Rae, Cambridge Univ. Press), and Embryonic Stem Cells: Methods and Protocols (K. Turksen ed., Humana Press). Other texts include Creating a High Performance Culture (Aroselli, Hu. Res. Dev. Pr. 1996) and Limits to Growth (D. H. Meadows et al., Universe Publ. 1974). Tissue culture supplies and reagents are available from commercial vendors such as Gibco/BRL, Nalgene-Nunc International, Sigma Chemical Co., and ICN Biomedicals.

Although this specification provides guidance to one of ordinary skill in the art, reference to technical literature, mere reference does not constitute an admission that the technical literature is prior art.

In the broadest aspect of the present invention there is provided a method of producing an implantable collagen-containing medical device comprising the step of coating said collagen-containing medical device with metal microparticles and/or metal nanoparticles, wherein said step of coating said collagen-containing medical device is by sonication such that the collagen-containing medical device has anti-bacterial and anti-inflammatory properties on implantation compared to the medical device not coated with metal microparticles and/or metal nanoparticles.

The purpose of the metal microparticles and/or metal nanoparticles is to prevent and/or treat bacterial infection and/or prevent and/or treat inflammation. Accordingly, a metal that has been shown previously to have anti-bacterial and/or anti-inflammatory properties are encompassed in the present invention. Preferably, the metal microparticles and/or metal nanoparticles comprise metals selected from the group consisting of silver and copper or combinations thereof.

The term collagen as used herein refers to all forms of collagen, including those which have been processed or otherwise modified. Preferred collagens are treated to remove the immunogenic telopeptide regions ("atelopeptide collagen"), are soluble, and will have been reconstituted into fibrillar form.

The collagen-containing medical device can comprise a matrix, a membrane, a microbead, a fleece, a thread, or a gel, and/or mixtures thereof. In some embodiments the collagen-containing medical device comprises a type I/III collagen matrix (ACI Matrix™), small intestinal submucosa (Vitrogen™) or collagen membrane (CelGro™ Orthocell Pty Ltd).

The term collagen-containing membrane refers to a piece or segment of collagen-containing tissue that has been produced by methods known in the art and disclosed, for example, in U.S. Pat. No. 9,096,688. The collagen-containing membrane can be any geometric shape but is typically substantially planar and may, in position, conform to the shape of underlying or overlying surface.

The collagen-containing membrane preferably has the following properties:

a) pores that interconnect in such a way as to favour tissue integration and vascularisation;
b) biodegradability and/or bioresorbability so that normal tissue ultimately replaces the collagen-containing membrane;
c) surface chemistry that promotes cell attachment, proliferation and differentiation;
d) strength and flexibility; and
e) low antigenicity.

The collagen-containing membrane is typically prepared or manufactured from "collagen-containing tissue" comprising dense connective tissue found in any mammal. The term "collagen-containing tissue" means skin, muscle and the like which can be isolated from a mammalian body that contains collagen. The term "collagen-containing tissue" also encompasses "synthetically" produced tissue in which collagen or collagen containing material has been assembled or manufactured outside a body.

In some embodiments, the collagen-containing tissue is isolated from a mammalian animal including, but not limited to, a sheep, a cow, a pig or a human. In other embodiments, the collagen-containing tissue is isolated from a human.

In some embodiments, the collagen-containing tissue is "autologous", i.e. isolated from the body of the patient in need of treatment.

In some embodiments, the collagen-containing membrane will comprise greater than 80% type I collagen. In other embodiments, the collagen-containing membrane will comprise at least 85% type I collagen. In still other embodiments the collagen-containing membrane will comprise greater than 90% type I collagen.

The collagen-containing membrane may be manufactured by any method known in the art; however, one preferred method includes the following steps:

(i) isolating a collagen-containing tissue and incubating the tissue in an ethanol solution;
(ii) incubating the collagen-containing tissue from step (i) in a first solution comprising an inorganic salt and an anionic surfactant in order to denature non-collagenous proteins contained therein;
(iii) incubating the collagen-containing tissue produced in step (ii) in a second solution comprising an inorganic acid until the collagen in said material is denatured; and
(iv) incubating the collagen-containing tissue produced in step (iii) in a third solution comprising an inorganic acid with simultaneous mechanical stimulation for sufficient time to enable the collagen bundles in said collagen-containing tissue to align;

wherein the mechanical stimulation comprises applying tension cyclically to the collagen-containing tissue.

It will be appreciated that any inorganic salt may be used in the first solution as long as it is capable of forming a complex with Lewis acids. In some embodiments, the inorganic salt is selected from the group consisting of trimethylammonium chloride, tetramethylammonium chloride, sodium chloride, lithium chloride, perchlorate and trifluoromethanesulfonate. In other embodiments, the inorganic salt is lithium chloride (LiCl).

While any number of anionic surfactants may be used in the first solution, in some embodiments, the anionic surfactant is selected from the group consisting of alkyl sulfates, alkyl ether sulfates, alkyl sulfonates, and alkyl aryl sulfonates. Particularly useful anionic surfactants include alkyl sulphates such as sodium dodecyl sulphate (SDS).

In some embodiments, the first solution comprises about 1% (v/v) SDS and about 0.2% (v/v) LiCl.

In some embodiments, the inorganic acid in the second solution comprises about 0.5% (v/v) HCl, while the inorganic acid in the third solution comprises about 1% (v/v) HCl.

It will be appreciated by those skilled in the art that the incubation periods in each of the three steps will vary depending upon: (i) the type of collagen-containing tissue; (ii) the type of inorganic salt/acid and/or anionic surfactant; (iii) the strength (concentration) of each inorganic salt/acid and/or anionic surfactant used and (iv) the temperature of incubation. In some embodiments, the incubation period in step (i) is at least 8 hours. In other embodiments, the incubation period in step (ii) is less than 60 minutes, while in other embodiments the incubation period in step (iii) is at least 20 hours.

In some embodiments, the incubation in step (ii) is at about 4° C. In other embodiments, the incubation in step (ii) is undertaken for at least 12 hours.

In some embodiments, the second solution comprises about 0.5% (v/v) HCl.

In some embodiments, the incubation in step (iii) is undertaken for about 30 minutes. In other embodiments, the incubation in step (iii) is undertaken with shaking.

In some embodiments, the third solution comprises about 1% (v/v) HCl solution.

In some embodiments, the incubation in step (iv) is undertaken for about 12 to 36 hours, preferably for about 24 hours. In other embodiments, the incubation in step (iv) is undertaken with shaking.

In some embodiments, the method further comprises a neutralization step between step (iii) and step (iv) which comprises incubation of said collagen-containing tissue with about 0.5% (v/v) NaOH.

In some embodiments, the method further comprises step (v) which comprises incubating the collagen-containing tissue from step (iv) with acetone and then drying the collagen-containing tissue.

In some embodiments, the method further comprises between steps (ii) and (iii) and/or between steps (iii) and (iv) a step of contacting the collagen-containing tissue with glycerol in order to visualise and facilitate the removal of fat and/or blood vessels.

The glycerol maybe contacted with the collagen-containing tissue for any amount of time that will facilitate the removal of fat and/or blood vessels. In some embodiments, the contact time is at least 10 minutes.

In some embodiments, the method further comprises between steps (ii) and (iii) and/or between steps (iii) and (iv) a wash step for the collagen-containing tissue. The purpose of the wash step used between steps (ii) and (iii) is to remove denatured proteins. Thus, any wash solution capable of removing denatured proteins can be used. In some embodiments the wash solution used between steps (ii) and (iii) is acetone.

Following the washing with acetone, the collagen-containing tissue is further washed with sterile water.

In some embodiments, the collagen-containing tissue is further washed in a NaOH:NaCl solution. If the collagen-containing tissue is washed with NaOH:NaCl it is then preferably washed with sterile water.

In some embodiments, after step (iv) the collagen-containing tissue is further washed with the first solution.

The term "simultaneous mechanical stimulation" used in the methods described herein refers to the process of stretching the collagen-containing tissue during the chemical processing of the collagen-containing tissue. The collagen-containing tissue may undergo static and/or cyclic stretching. Accordingly, in some embodiments the simultaneous mechanical stimulation may comprise:
(i) stretching of the collagen-containing tissue for a preset period;
(ii) relaxation of the collagen-containing tissue for a preset period; and
(iii) n-fold repetition of steps (i) and (ii), where n is an integer greater than or equal to 1.

If the mechanical stimulation is carried out by stretching the collagen-containing tissue, the collagen-containing tissue is preferably stretched along its long axis.

In some embodiments, the simultaneous mechanical stimulation comprises applying tension cyclically to collagen-containing tissue, wherein the periodicity of the tension comprises a stretching period of about 10 seconds to about 20 seconds and a relaxing period of about 10 seconds, and the strain resulting therefrom is approximately 10%, and the mechanical stimulation continues until the collagen bundles within the collagen-containing tissue are aligned as described herein.

Once produced the collagen-containing tissue comprises collagen fibres or bundles with a knitted structure. The term "knitted structure" as used herein refers to a structure comprising first and second groups of fibres or bundles where fibres or bundles in the first group extend predominately in a first direction and fibres or bundles in the second group extend predominately in a second direction, where the first and second directions are different to each other and the fibres or bundles in the first group interleave or otherwise weave with the fibres or bundles in the second group. The difference in direction may be about 90°.

The collagen-containing tissue made by the preferred methods comprise a "maximum tensile load strength" of greater than 20N. In some embodiments, the collagen-containing tissue of the present invention has maximum tensile load strength greater than 25N, 40N, 60N, 80N, 100N, 120N or 140N.

Further, it is believed that the knitted structure of the embodiments of the collagen-containing tissue provides reduced extension at maximum load of the collagen-containing patch while providing an increase in modulus.

The term "modulus" as used herein means Young's Modulus and is determined as the ratio between stress and strain. This provides a measure of the stiffness of the collagen-containing tissue and/or patch.

In some embodiments the collagen-containing tissue has a modulus of greater than 100 MPa. In other embodiments the collagen-containing tissue has a modulus of greater than 200 MPa, 300 MPa, 400 MPa, or 500 MPa.

The term "extension at maximum load" as used herein means the extension of the collagen-containing tissue at the maximum tensile load strength referenced to the original length of the collagen-containing tissue in a non-loaded condition. This is to be contrast with maximum extension which will be greater.

In some embodiments, the collagen-containing tissue has extension at maximum load of less than 85% of the original length.

Once the collagen-containing tissue has been produced it may then be shaped into a collagen-containing membrane for use. In some embodiments, the collagen-containing membrane is adapted by shaping the membrane to provide better means of manipulation in situ.

Preferably, the collagen-containing membrane of the present invention is sufficiently thick to provide support for cells; however, not too thick that the ability to manipulate the collagen-containing membrane in situ is impaired. Thus, in some embodiments the collagen-containing membrane is between 25 μm and 200 μm thick. In some embodiments, the collagen-containing membrane is between 30 μm and 180 μm thick. In other embodiments, the collagen-containing membrane is between 35 μm and 170 μm thick. In still other embodiments, the collagen-containing membrane is between 40 μm and 160 μm thick. In still other embodiments, the collagen-containing membrane is between 45 μm and 150 μm thick. In still other embodiments, the collagen-containing membrane is between 50 μm and 140 μm thick. In still other embodiments, the collagen-containing membrane is between 50 μm and 100 μm thick. Finally, in some embodiments the collagen-containing membrane is about 50 μm thick.

The collagen-containing membrane maybe used as the collagen-containing medical device or incorporated into the medical device. For example, the collagen-containing membrane can be used to cover a portion or all of the surface of a medical device. The medical device could be orthopaedic implant, dental implant, veterinary prosthetic device, a scaffold or a tissue engineering matrix.

The collagen-containing medical device is coated with metal microparticles and/or metal nanoparticles by sonication. Sonication refers to ultrasound >20 kHz. The methods disclosed herein may be performed using sonication at 20 kHz, 30 kHz, 40 kHz, 50 kHz, 60 kHz, 70 kHz, 80 kHz, 90 kHz, 100 kHz, 110 kHz, 120 kHz, 130 kHz, 140 kHz, 150 kHz, 160 kHz, 170 kHz, 180 kHz, 190 kHz, 200 kHz, or more, or a range comprising any combination therein.

In one embodiment, the collagen-containing medical device is contacted with inorganic metal such as Au, Ag, Fe, Co, Ni, Cu, Al or Zn in a solution of water and ethylene glycol (10:1 v/v). The reaction mixture is purged under Ar and irradiated with a high-intensity ultrasonic horn in a sonication bath such, for example, Sweep 200 H ultrasonic bath from SweepZone® Technology, operating at 50-60 kHz) under the flow of an Ar—$H_2$ mixture (95:5).

An aqueous solution of ammonia ($NH_4OH/AgNO_3$ molar ratio=2:1) may be added to the reaction during the first few minutes of sonication. The temperature is typically held around room temperature to about 30 C during the sonication. Following sonication, the coated collagen-containing medical device is washed in distilled water and agitated to remove any residual metal solution. The collagen-containing medical device can then be dried at room temperature.

Without wishing to be bound by theory, a nanoparticle refers to a particle with at least one dimension 0.5 nm to 100 nm. Without wishing to be bound by theory, a microparticle refers to a particle with at least one dimension 100 nm to 1000 nm. As will be appreciated by the person skilled in the art, however, there may be overlap in these size distributions. Thus, the metal microparticles and/or metal nanoparticles may have a size of about, or ±10%, 0.5 nm, 1 nm, 5 nm, 10 nm, 15 nm, 20 nm, 25 nm, 30 nm, 40 nm, 45 nm, 50 nm, 55 nm, 60 nm, 65 nm, 70 nm, 75 nm, 80 nm, 85 nm, 90 nm, 95 nm, 100 nm, 150 nm, 200 nm, 300 nm, 400 nm, 500 nm, 600 nm, 700 nm, 800 nm, 900 nm, 1000 nm, or a range comprising any combination therein.

In one embodiment, the metal microparticles and/or metal nanoparticles may have a size range from about 0.5 nm to about 500 nm. In one embodiment, the metal microparticles and/or metal nanoparticles may have a size of about 70 nm.

Microparticle and/or nanoparticle size may be determined by microscopy, for example electron microscopy.

In some embodiments, the collagen-containing medical device is further coated using natural or synthetic polymer, metal, metal oxide, oxide, metal nitride, borate, ceramic, zirconia, allograft hard tissue, allograft soft tissue, xenograft hard tissue, xenograft soft tissue, carbon nanostructure, carbon, glasses, natural or biocompatible material.

The coating of metal microparticles and/or metal nanoparticles is capable of performing at least one of treating infection; preventing infection; treating inflammation; preventing inflammation; promoting cell adhesion; preventing biofilm formation; inhibiting biofilm formation; promoting cell proliferation; promoting binding with a biological or non-biological system; increasing or decreasing a cell function; delivering a drug and/or bioactive agent, or ensuring a better integration of a material into the host tissue.

The implantable collagen-containing medical device can be delivered to a host organism by any suitable method known in the art. For example, and in no way limiting, an implantable collagen-containing medical device can be delivered by direct surgical placement or topical application. Delivery can be directed to any cell type or tissue in any mammalian animal.

Specific examples are presented below of methods. They are exemplary and not limiting.

EXAMPLES

Example 1—Preparation of Silver-Coated Collagen Membrane

CelGro™ collagen membrane that has been approved for CE mark on dental guided bone regeneration was obtained from Orthocell Ltd, Australia. Silver 70 nm nanoparticle stock solution was purchased from Suzhou ColdStones Technology Co., Ltd. (Jiangsu, China).

Sonication coating: The stock AgNP solution containing 20 mg/mL 70 nm silver nanoparticle was diluted to 0.6, 0.8, 1.0 and 1.2 mg/mL. Collagen membranes were trimmed to 1.0, 1.5, or 2.0 cm squares depending on the test to follow. All the chemical reagents of chemical grade were purchased from Sigma-Aldrich (Steinheim, Germany) and used without further purification.

Several parameters were used to obtain the best conditions for the coating of silver nanoparticles on the collagen membrane: the ultra-sound power, solution temperature, reaction time, and concentrations of the reagents. Results representing a typical experiment were as follows. Collagen membranes were added to a 0.02M $AgNO_3$ solution of water and ethylene glycol (10:1 v/v) in a 100-mL sonication flask. The reaction mixture was then purged under Ar for 1 h to remove traces of 02/air and irradiated for 2 h with a high-intensity ultrasonic horn (Sweep 200 H ultrasonic bath from SweepZone® Technology, operating at 50-60 kHz) under the flow of an Ar—$H_2$ mixture (95:5).

A 25 wt % aqueous solution of ammonia ($NH_4OH$/$AgNO_3$ molar ratio=2:1) was added to the reaction slurry during the first 10 min of sonication. The sonication flask was placed in a cooling bath with a constant temperature of 30° C. during the sonication. Following sonication, the coated samples were immersed in distilled water and manually agitated for 20 seconds to remove any residual silver solution. The samples were then air dried for 24 hours at room temperature.

Sputtering coating: Sputtering AgNP-coated collagen membranes were fabricated by direct deposition through radio-frequency magnetron sputtering (Hummer BC-20 DC/RF Sputter System, AnatechUSA). A high purity Ag target (99.99%, Ezzi Vision Pty Ltd, Australia) was used as Ag source. Collagen membranes were fixed on a sample stage in the sputtering chamber with double-sided tape to ensure stability during sputtering (Jiang et al., Surface and Coatings Technology, 2010. 204(21-22): p. 3662-3667; Song et al., Thin Solid Films, 2011. 519(20): p. 7079-7085). The chamber was vacuum sealed overnight (approx. 10 h) to reach $3.0\times10^{-7}$ Torr prior to sputtering. Ar gas (99.99% pure) was purged into the chamber during the sputtering process with a flow rate of 20 sccm. The sputtering deposition was carried out at $1\times10^{-2}$ Torr with an applied DC power of 100 W for 10 min at 17° C. The working distance between collagen membrane specimens and Ag target was 12 cm.

Samples for scanning electron microscope (SEM) observation were cropped to the desired size (3*3 mm) and mounted on a stub. A layer of platinum was then sputtered on the samples, after which they were ready for SEM imaging using Zeiss55 at an accelerating voltage of 15 kV in Centre for Microscopy, Characterisation and Analysis, University of Western Australia (CMCA-UWA).

Light microscope images clearly demonstrated the structural characteristics of the bilayer collagen membrane: a “smooth” side consisting of well-orientated collagen fibers, and a “rough” side comprising randomly aligned collagen fibers (FIG. 1A). Furthermore, AgNP was evenly coated on both sides of the collagen membrane using sonication, but only one side was coated using sputtering technique (FIG. 1). SEM images revealed that higher AgNP concentrations resulted in greater deposition of AgNP on collagen fibers during sonication coating, however large and uneven amounts of AgNP were seen on collagen fibers using sputtering coating. AAS demonstrated that AgNP attached to collagen membrane by sputtering coating at significantly larger content than sonication coating, and the AgNP content increased with the increasing concentration of AgNP coating solution.

For measurement of AgNP content on coated collagen membrane, samples were cropped to the same size (1 $cm^2$) and placed into 1% nitric acid to dissolve the collagen substrate. The concentration of AgNP in nitric acid solution was measured using atomic absorption spectrometry (AAS).

For the released AgNP test, the weight of AgNP-coated collagen membrane was recorded, and the membrane immersed in 6 mL of 1×PBS solution. After 24 hours, 3 mL of solution was removed and stored, and 3 mL of fresh PBS solution was added to the original solution containing the coated membrane. The mixture was then shaken. These two steps were repeated for six consecutive days, where 3 mL of silver-PBS solution was removed and replaced by 3 mL of fresh PBS solution each time. On day seven, the coated membrane was removed from the PBS solution. The content of released AgNP was tested by AAS. Calibration solutions containing 0, 0.5, 1.0, 1.5, 2.0, and 3.0 ppm silver ions in PBS solution were used. After adjusting the hollow cathode (HC) lamp, deuterium (D2) lamp, and flame for maximum absorption sensitivity, the calibration solutions were tested, and silver concentrations recorded (Kulthong et al., 2010, Particle and fibre toxicology, 7(1): p. 8). The concentration of released AgNP in PBS was calculated as a weight percentage of the coated membrane. The peak released AgNP concentration in culture medium (on day 1) was selected, and this AgNP-containing culture medium was used for the cytotoxicity test.

Example 2—Testing of Metal Coated Collagen Membrane

Anti-Bacterial Effectiveness Test

McFarland turbidity standards from 0.5 to 10.0 were prepared using a mixture of test organism and suitable broth. After visual comparison, 0.5 McFarland turbidity standard was selected for anti-bacterial testing. To prepare the agar plate, 15 ml lysogeny broth (LB) agar was poured into each Petri dish and allowed to solidify. Aliquots of 100 μl *Staphylococcus aureus* (*S. aureus*) (strain: ATCC 6538P) or *Pseudomonas aeruginosa* (*P. aeruginosa*) (strain: ATCC 9027) bacterial suspensions were distributed evenly on the surface of the solid LB agar and allowed to settle. Sonication AgNP-coated collagen membranes and sputtering AgNP-coated collagen membranes, both in different silver concentrations, were cropped into round shape with the same 5 mm diameter and placed on the surface of the bacterial suspension covered LB agar. Uncoated collagen membrane was treated as the control. The LB agar-bacterial-AgNP-coated collagen membrane plates were incubated at 37° C. for 96 hours, and the zone of inhibition was measured every 24 hours as the area ($mm^2$) of no bacterial growth around each membrane.

Figure 2:
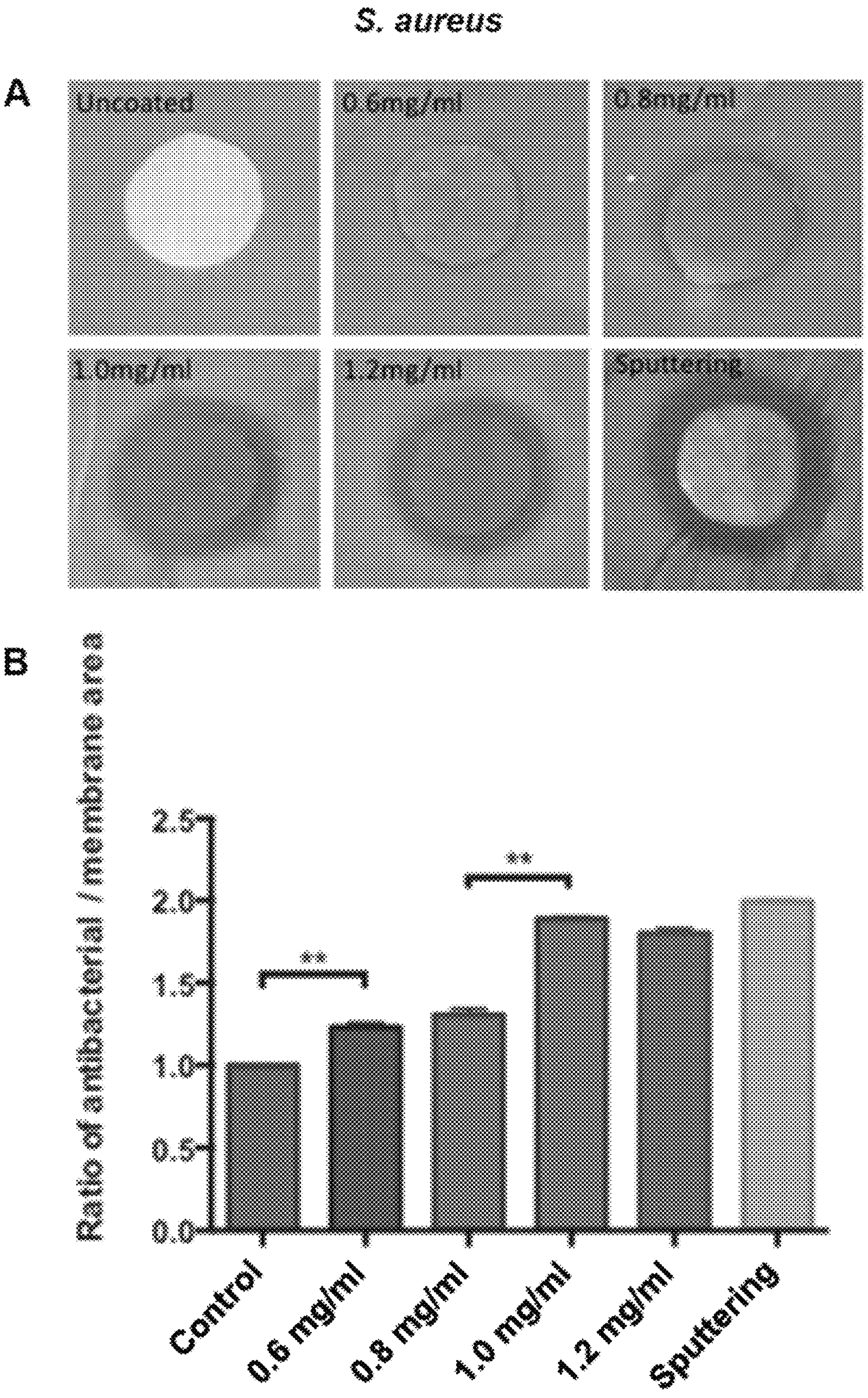
FIG. 2. Anti-bacterial effect of AgNP-coated collagen membrane on *S. aureus* and *P. aeruginosa*. The anti-bacterial effect of AgNP-coated collagen membrane on *S. aureus* and *P. aeruginosa* (A, C) and the quantitative results based on the ratio of anti-bacterial area to membrane area (B, D). (n=3; mean±SD; *p<0.05, **p<0.005)
Figure 2:
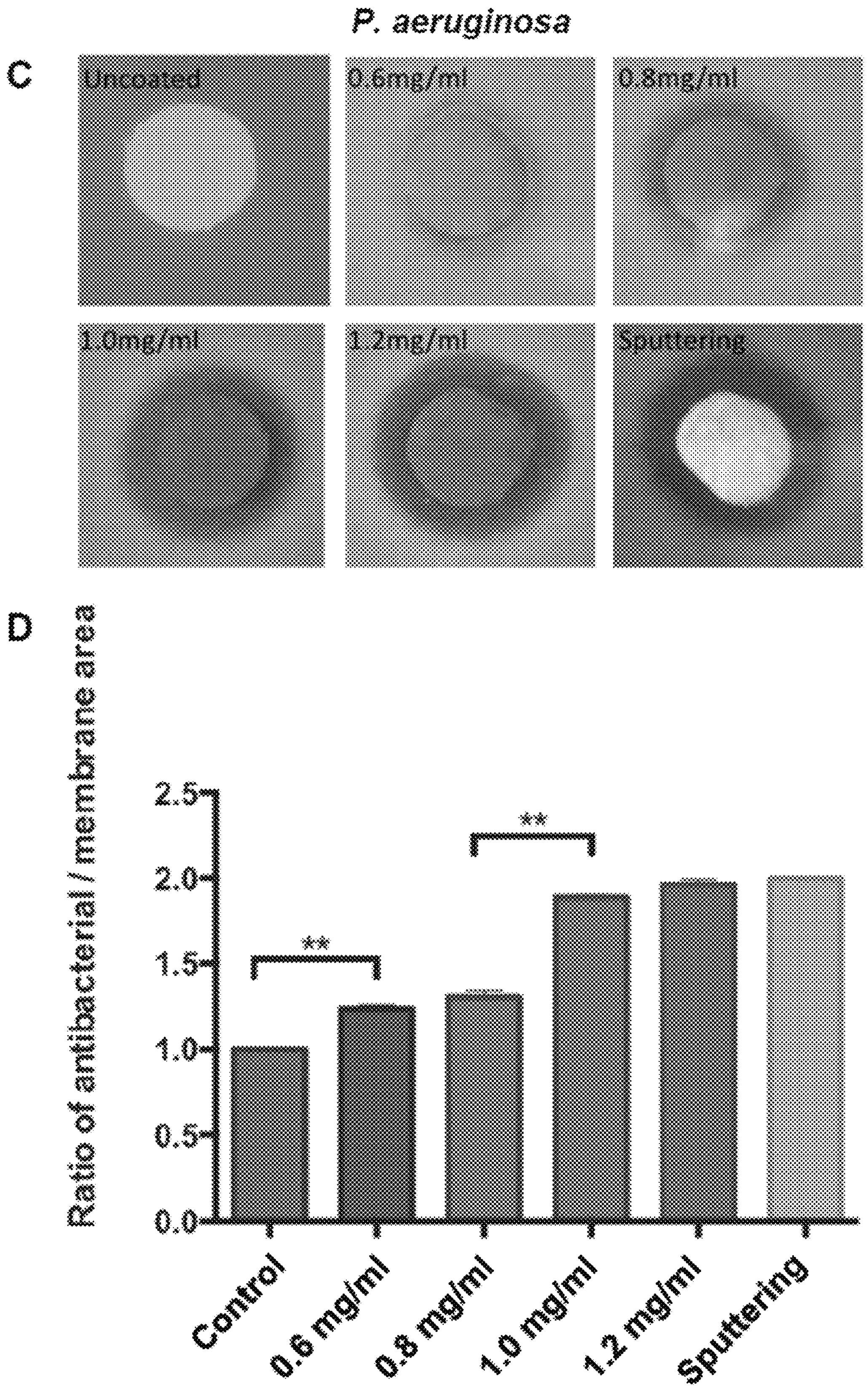

AgNP-coated collagen membranes created by sonication in different concentrations of AgNPs or by sputtering were placed on bacterial inoculation plates to test anti-bacterial properties. The anti-bacterial effects of AgNP on *S. aureus* and *P. aeruginosa* were measured by the quantification of the growth inhibition zone surrounding the coated collagen membrane (FIG. 2). After four days culture, AgNP-coated collagen membranes produced by sonication showed increasing anti-bacterial effect with AgNP content across the range 0.6 mg/mL to 1.0 mg/mL. Interestingly, membrane coated by sonication at 1.0 mg/mL and 1.2 mg/mL AgNP solution exhibited similar anti-bacterial effects as those coated by sputtering (FIG. 2).

Cell Culture

C3H101/2 cells were used to test for cell toxicity and viability while RAW264.7 cells were used to measure the cytokine release. Both cell lines were incubated at 37° C. in a humidified atmosphere containing 5% $CO_2$. C3H101/2 cells were cultured in Minimal Essential Medium (MEM alpha, Gibco®) supplemented with 10% fetal bovine serum (FBS, Gibco®) and 1% streptomycin and penicillin mixture. RAW264.7 cells were cultured in Dulbecco's Modified Eagle Medium (DMEM+GlutaMAX™-I) supplemented with 10% fetal bovine serum (FBS, Gibco®) and 1% streptomycin and penicillin mixture.

Figure 3:
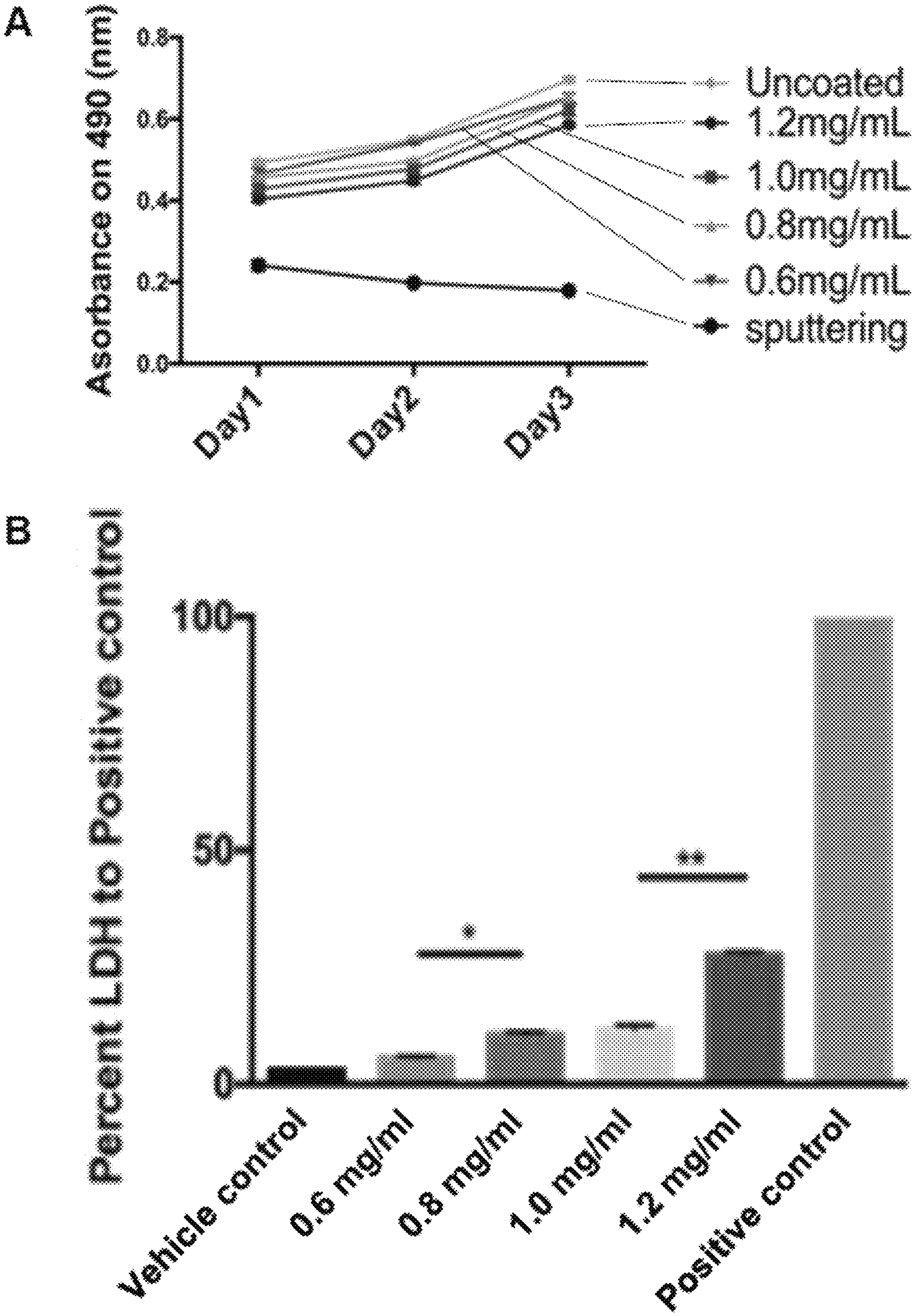
FIG. 3. In vitro cytotoxicity assessment and AgNPs released test. MTS testing of C3H10 cells cultured on AgNPs-coated collagen membrane by sonication and sputtering, and uncoated collagen membrane over a period of 3 days (A). LDH leakage assay of C3H10 cells on AgNPs-coated membrane (B). Content of AgNPs released in aqueous phase accessed by AAS and calculated as the percentage of weight of coated membrane (C). MTS testing of C3H10 cells cultured on uncoated collagen membrane in released AgNPs (D). SEM images (×120K) showed the uncoated and AgNPs-coated collagen membrane. Cell growth and proliferation on AgNPs-coated collagen membrane was visualized by CLSM (cell skeleton indicated by F-actin, AgNPs-coated or uncoated membrane indicated by green fluorescence and cell nuclei indicated by DAPI).
Figure 3:
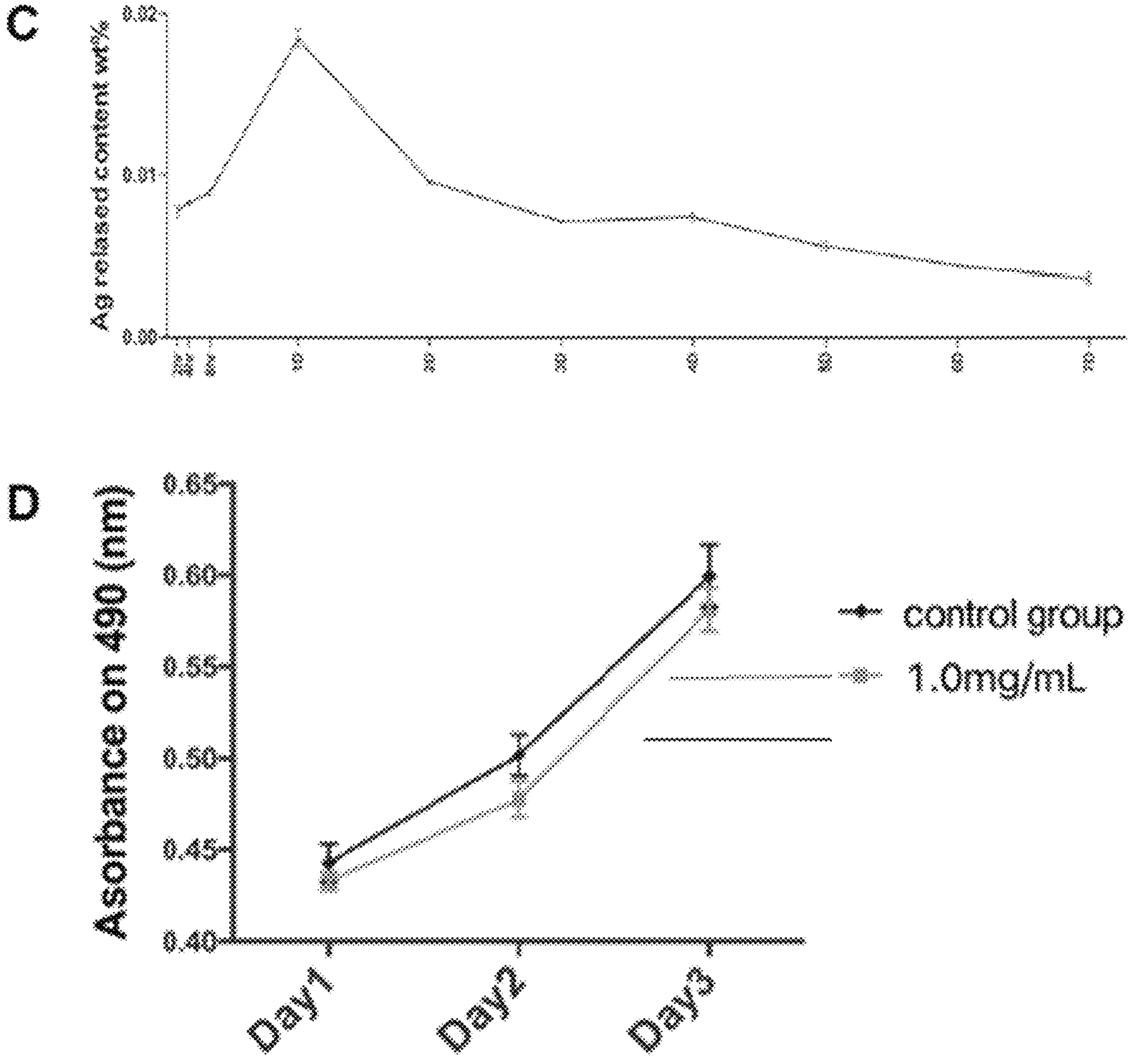

C3H10 cells were seeded on AgNP-coated collagen membranes, and cell proliferation and cell membrane integrity were assessed by MTS test and lactate dehydrogenase (LDH) leakage assay, respectively. After 24 hours in culture, there was a decline in cell numbers which was AgNP-dose dependent, however proliferation rates after Day 1 were similar (FIG. 3A). On the other hand, collagen coated with silver by the sputtering method showed severe inhibition of cell growth, suggesting that this coating technique is not suitable for the fabrication of AgNPs-collagen structure for cell proliferation (FIG. 3A). Cell membrane integrity was assessed by LDH leakage assay. After 24 hours culture, there was an increase in the amount of leaked LDH which correlated to the concentration of AgNP used on coated collagen membrane, and there is a significant difference between 1.0 and 1.2 mg/mL sonication groups, indicating that AgNPs can cause damage to the cell membrane (FIG. 3B). AgNP-coated collagen membrane in 1.0 mg/mL AgNP solution was selected as the functional dose for the following tests, taking into consideration antibacterial effectiveness and minimal cytotoxicity.

To determine whether the amount of AgNPs released from the collagen membrane can cause cytotoxicity, the released AgNPs from 1.0 mg/mL sonication coated collagen membrane in PBS was determined by AAS (FIG. 3C). The highest released amount of AgNPs was recorded at 24 hours ($1.86*10^{-6}$ mg/mL), and such amount of the released silver nanoparticles was less than 0.02% wt of the coated collagen membrane. After 24 hours, the released silver nanoparticles were decreased gradually. In order to assess the cytotoxicity of released AgNPs, the highest concentration of released silver was selected to test cell proliferation in culture medium supplemented by AgNPs (final concentration is $1.86*10^{-6}$ mg/mL as AAS indicated) and examined by MTS testing. No inhibition of cell growth was observed (FIG. 3D).

Confocal laser scanning microscopic images showed that cells seeded on AgNP-coated collagen membrane demonstrated no obvious morphological differences compared with cells on uncoated collagen membranes.

MTS Test and LDH Release Assay

In this study, C3H10 cells were used to test cell proliferation and cell viability (Vangsness et al., Clinical orthopaedics and related research, 1997, 337: p. 267-271). To evaluate the cytotoxicity of released AgNP from AgNP-coated collagen membrane, C3H10 cells were seeded on AgNP-coated collagen membrane (1 cm diameter) at a density of $3\times10^3$ cells per membrane (1 cm diameters) and were incubated for 24 hours for attachment. To evaluate the cytotoxicity of released AgNP from sonication coated membrane, C3H10 cells were seeded on uncoated collagen membrane (1 cm diameters) at a density of $3\times10^3$ cells per membrane and cultured in a medium supplemented by AgNP at a final concentration of $1.86\times10^{-6}$ mg/mL.

The MTS tests were performed with the CellTiter®96 AQueous Non-Radioactive Cell Proliferation Assay kit (Promega, USA). The kit is based on bio-reduction of substrate [3-(4,5-dimethylthiazol-2-yl)-5-(3-carboxymethoxyphenyl)-2-(4-sulfophenyl)-2H-tetrazolium (MTS) into a brown formazan that is produced by dehydrogenase enzymes in metabolically active cells (Cory et al., Cancer communications, 1991. 3(7): p. 207-212; Salih et al., Journal of Materials Science: Materials in Medicine, 2000, 11(10): p. 615-620; Salgado et al., Materials Science and Engineering, 2002, 20(1): p. 27-33). The MTS solution was added to each well after 24 hours incubation. This was followed by a further three hours incubation at 37° C. in a humidified atmosphere containing 5% $CO_2$ in the dark, after which time the optical density (OD) was measured by a 96-well plate reader (Bio-Rad, Model 680, USA) at 490 nm wavelength.

Assessment of cell membrane integrity by LDH release assay in C3H10 cells was performed. Cells were seeded on AgNP-coated collagen membrane. LDH released was measured after 24 hours culture according to the instructions for the CytoTox 96® Non-Radioactive Cytotoxiciy Assay Kit (Promega USA). The OD of collected culture medium was read by a 96-well plate reader (Bio-Rad, Model 680, USA) at 490 nm wavelength.

Macrophage cell line RAW264.7 was used in enzyme-linked immunosorbent assay (ELISA). Cells were seeded on AgNP-coated collagen membrane and allowed 24 hours for attachment. Cells were then challenged with lipopolysaccharide (LPS) at 100 ng/ml, and supernatants from cell cultures were collected at different times (0 hours, 2 hours, 4 hours and 8 hours) and analyzed. Cells seeded on coated and uncoated membrane without LPS challenge acted as controls. The production of TNF-alpha and interleukin-6 (IL-6) were measured using the mouse TNF-alpha ELISA kit and mouse IL-6 ELISA kit (Novex®, ThermoFisher Scientific, USA). Briefly, standards and samples were diluted in assay diluent. Standard, samples and control (100 μl each) were added into the appropriate wells. The plates were sealed and incubated for 2 hours at room temperature. After incubation, detector antibody (100 μl, MS Biotin Conjugate solution) was applied and incubated for 30 minutes at room temperature. Streptavidin-HRP reagents (100 μl) were added into each plate after washing and incubated for 30 minutes at room temperature. After washing, Stabilized chromogen (100 μl) was performed in each well and incubated for 30 minutes at room temperature in the dark. Stop solution (50 μl) was used to terminate the reaction in each well, with absorbance was read at 450 nm.

Figure 4:
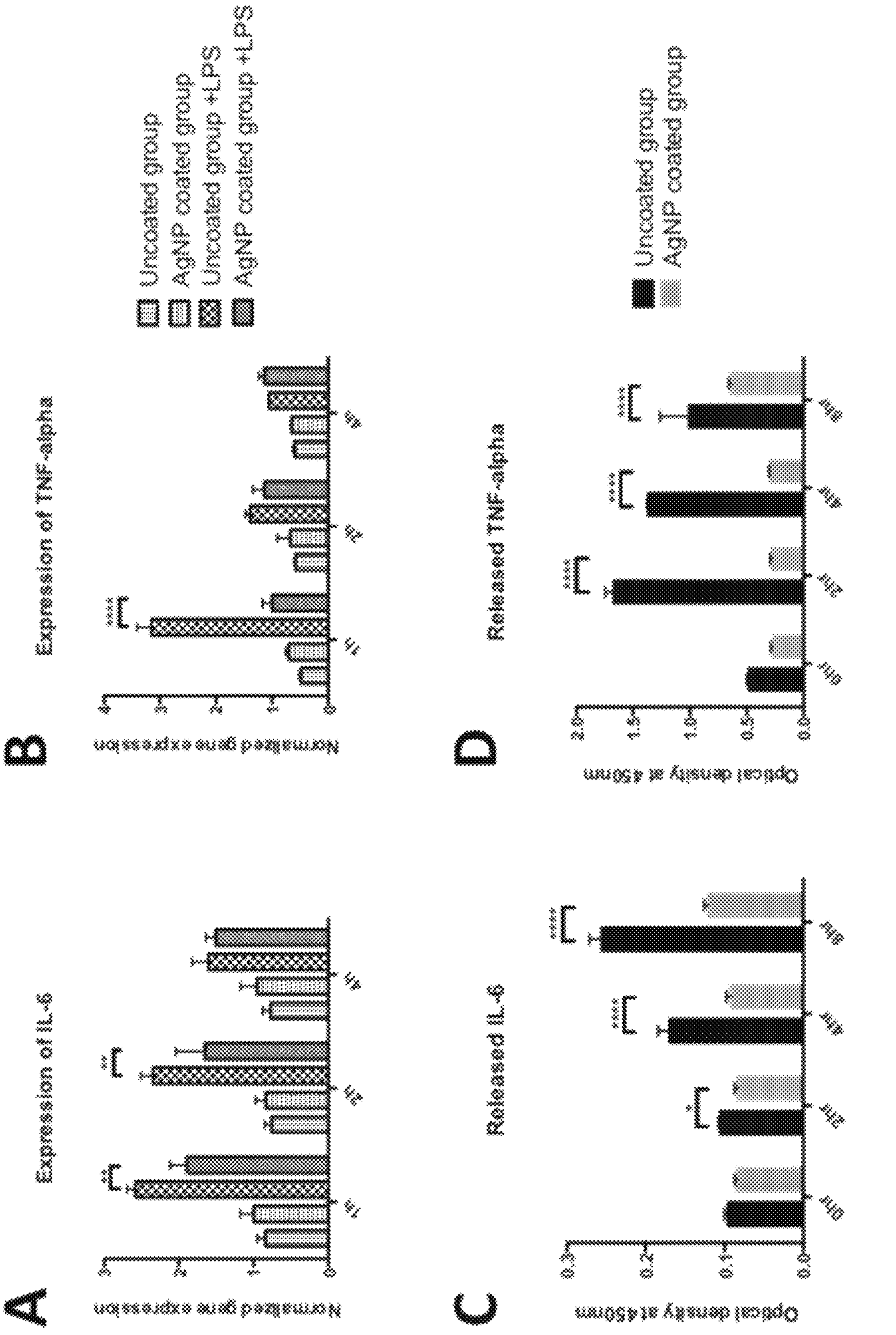
FIG. 4. Anti-inflammation effect of AgNPs-coated collagen membrane. The gene expression of IL-6 and TNF-alpha of RAW264.7 cell after challenge by LPS (A, B). The secretion of IL-6 and TNF-alpha of RAW264.7 after challenge by LPS (C, D). (n=3; means±SD; *p<0.05, p<0.005, *p<0.0005, ****p<0.0001).

The anti-inflammatory effect of AgNP-coated collagen membrane was investigated further by q-PCR & ELISA. There was no significant difference in the gene expression of IL-6 and TNF-alpha of RAW264.7 cells seeded on AgNP-coated and uncoated collagen membranes without LPS stimulation (FIG. 4A, B). When stimulating cells with LPS, gene expression of IL-6 on AgNPs-coated collagen membrane was lower in comparison with the uncoated group 1 hour and 2 hours after LPS stimulation, however expression of TNF-alpha was only suppressed 1 hour after (FIG. 4A, B). ELISA results revealed that released IL-6 and TNF-alpha are further suppressed 2 hours, 4 hours and 8 hours after LPS stimulation (FIG. 4C, D).

Figure 5:
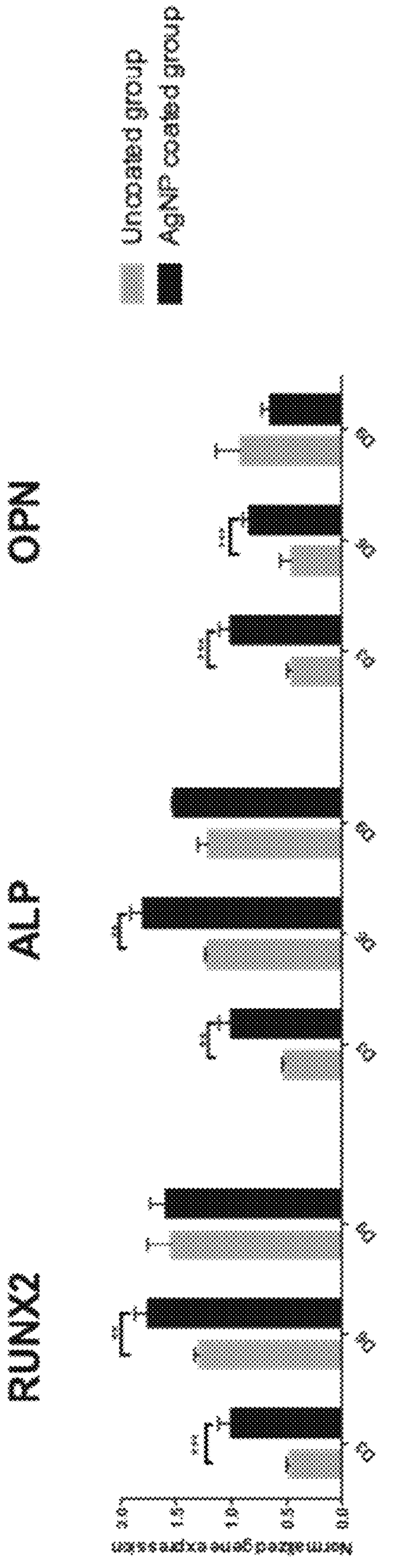
FIG. 5. Cell differentiation on AgNPs-coated collagen membrane. Osteogenic markers expression (RUNX2, ALP and OPN) of C3H10 cells after 3 days, 6 days and 9 days culture, showing the significantly increased expression at 3 and 6 days in AgNP coated group. (n=3; means±SD; *p<0.05, p<0.005, *p<0.0005, ****p<0.0001.)

To examine the effect of osteogenesis in vitro of AgNP-coated collagen membranes, C3H10 cells were seeded on AgNP-coated collagen membranes and the osteogenic profile was tested by q-PCR. As shown in the FIG. 5, AgNP-coated collagen membranes induced osteogenic differentiation of C3H10 cells. The expression of early osteogenic markers including RUNX, ALP and OPN were remarkably higher in cells cultured on the AgNP-coated membrane compared to the uncoated membrane at day 3 and 6, however there was no significant difference when cells continued to be cultured to day 9 (FIG. 5).

Example 3—Quantitative Real-Time Polymerase Chain Reaction (Q-PCR)

Total RNA was isolated from cultured C3H101/2 cells using PureLink™ RNA Mini Kit (Invitrogen, ThermoFisher Scientific, USA) according to the manufacturer's instructions. Complementary DNA (cDNA) was synthesised using QuantiTec Reverse Transcription kit (Qiagen). Real-time PCR was performed using iQ™ SYBR® Green Supermix according to manufacturer's instructions. Relative gene expression levels for osteogenesis (RUNX2, ALP, OPN) were obtained by normalizing them to the housekeeping gene (36B4). For the inflammatory cytokine gene expression test, RAW264.7 cells seeded on AgNP-coated membrane were challenged with LPS at 100 ng/ml ahead in 1 hour, 2 hours and 4 hours. RNA extraction, cDNA synthesis and q-PCR were performed as described above. The expression levels of TNF-alpha and IL-6 were obtained and normalized to housekeeping gene (36B4). Primers for the selected genes are listed in Table 1.

TABLE 1

| Gene | Primer sequence | |
|---|---|---|
| | Forward 5'-> 3' (SEQ ID NO) | Reverse 5'-> 3' (SEQ ID NO) |
| RUNX2 | GCCGGGAATGATGAGAAC TA (1) | GGACCGTCCACTGTCACTT T (2) |
| ALP | GAAGCTCTGGGTGCAGGA TAG (3) | TGTGTTTCCCAGGAGAGAA TG (4) |
| OPN | CCCGGTGAAAGTGACTGA TT (5) | TTCTTCAGAGGACACAGCA TTC (6) |
| TNF-alpha | CCCTCACACTCAGATCAT CTTCT (7) | GCTACGACGTGGGCTACAG (8) |
| IL-6 | CTGCAAGAGACTTCCATC CAG (9) | AGTGGTATAGACAGGTCTG TTGG (10) |
| 36B4 | CTTCCCACTTGCTGAAAA GG (11) | CGAAGAGACCGAATCCCAT A (12) |

Abbreviations:
RUNX2, runt-related transcription factor 2;
ALP, alkaline phosphatase;
OPN, osteopotin;
TNF-alpha, tumour necrosis factor alpha;
IL-6, interleukin 6.

Confocal Laser Scanning Microscopic Analysis

The adherent cell growth and proliferation on AgNP-coated collagen membrane were visualized by confocal laser scanning microscopic images. C3H101/2 cells were seeded on AgNP-coated collagen membranes in a 96-well plate at a cell density of $3.0*10^4$ viable cell per $cm^2$. After 24 hours incubation, the membranes were gently washed three times with PBS. 4% paraformaldehyde was used for cell fixation (20 minutes at room temperature), followed by three PBS washes. The cytoskeletons were stained with rhodamine phalloidin (5 units/mL; Biotium, USA) for 30 minutes in the dark. After three more PBS washes, nuclei were stained with Hoechst (Molecular Probes, Eugene, USA) for 15 minutes in the dark followed by three PBS washes. All the specimens were visualised by confocal laser scanning microscopy (CLSM; Nikon A1, Nikon, Japan).

Statistical Analysis

All data are presented as mean±standard deviation. Statistical analysis consisting of one-way analysis of variance (ANOVA) was performed to determine significant differences between the groups, and $p<0.05$ was considered to be significant.

DISCUSSION

Osseous integration and the prevention of infection are of prime importance in alveolar bone reconstruction. In this study, two barrier membranes coupled with anti-bacterial and anti-inflammatory properties were developed and the efficacy of two coating methods for generating AgNP-coated collagen membrane evaluated. Sonication of collagen membrane with AgNPs solution was found to effectively generate a membrane with even distribution and controllable deposition. The coating concentration was finalized by assessing anti-bacterial effect against cytotoxicity. The AgNP-coated collagen membrane developed in this study exhibited the potential to guide bone regeneration and an excellent anti-bacterial effect against two tested bacteria *S. aureus* and *P. aeruginosa*, as well as demonstrating effective anti-inflammatory and osteogenic induction abilities.

Sonication coating was carried out by high radiation ultrasound, allowing free suspended AgNPs to be infiltrated into the collagen membrane. Sputtering coating introduced an argon gas collision with pure silver target, resulting in the emission of AgNPs from the silver target to be directed onto the collagen membrane. AgNP solution concentration in sonication was controllable, allowing control of AgNP deposition on the collagen membrane. In contrast, sputtering coating was difficult to control as the procedure is very fast, a major limitation with regards to AgNP concentration control as AgNP deposition was too high. Generally, SEM showed successful coating of AgNPs on collagen membranes by both sonication and sputtering methods.

*Staphylococcus aureus* (Gram+) and *Pseudomonas aeruginosa* (Gram-) are two common pathogens in infectious diseases and *S. aureus* accounts for certain proportion of pathogens postoperatively in alveolar bone implant. In the study herein, coated collagen membrane fabricated via either sonication or sputtering exhibited excellent antibacterial effect towards these two strains of bacteria. Interestingly, the antibacterial effect was AgNPs-dependent in a certain range and it reached maximum when the coating concentration was 1.0 mg/ml. The results indicated that minimum functional coating can be achieved by sonication coating.

The results showed that in the sonication group, cell proliferation rates were not affected by AgNPs during 3 days with only initial cell membrane damages in 24 hours. However, AgNP-coated collagen membrane via sputtering exhibited extremely high cell growth inhibition. We presumed that the damage of the cell membrane structure occurring within 24 hours might be due to the attachment of the cells to the AgNP-coated surface. Moreover, small amounts of released AgNPs from coated collagen membrane had negligible cytotoxicity and this showed that the local administration of AgNP-coated collagen membrane will not have a detrimental influence on surrounding tissues. To achieve the highest anti-bacterial effect and lower cytotoxicity, 1.0 mg/mL sonication coating was selected as the coating condition. Normal cell morphology and cell cluster can be visualized by confocal laser scanning microscope, and this showed the potential of the tissue ingrowth into AgNP-coated collagen membrane.

After bone substitute placement, inflammations induced by infection or the bone graft tend to contribute to poor bone integration and finally less reliable preparation for tooth implant. The long-term presence of inflammatory cytokines like TNF-alpha and IL-6 may lead to over-activity of matrix metalloproteinases resulting in extracellular matrix degradation. IL-6 is a potent stimulator of fibroblast proliferation and there is evidence to suggest that exogenous IL-6 may have a role in scar formation, which can have adverse impact on bone integration process. TNF-alpha, a primary mediator in the systemic responses to sepsis and infection, can cause tissue injury when produced in excessive quantities. Collectively, over-active inflammation either caused by infection or host response to bone graft can have adverse impact postoperatively. It was shown that the AgNP-coated collagen membranes exhibited significant inhibition of TNF-alpha and IL-6 in both gene expression and protein release via q-PCR and ELISA, demonstrating its anti-inflammatory properties. Hence, in many infection conditions coupled with over-active inflammation, AgNP-coated collagen have the bimodal effect to fight against infections and ease inflammation at the same time, and this will be possible to reduce the risk of infection or graft induced inflammation after alveolar bone reconstruction.

In addition, AgNP-coated collagen membranes had a superior ability to induce osteogenic differentiation compared to uncoated membrane controls.

The invention claimed is:

1. A method of producing an implantable collagen-containing membrane comprising the step of coating said collagen-containing membrane with metal nanoparticles, wherein said step of coating said collagen-containing membrane is by sonication in a sonication bath to cause the metal nanoparticles to deposit and adhere onto a surface of the collagen-containing membrane such that the collagen-containing membrane has anti-bacterial and anti-inflammatory properties on implantation compared to the membrane not coated with metal nanoparticles.

2. A method according to claim 1, wherein the metal nanoparticles comprise metals selected from the group consisting of silver and copper or combinations thereof.

3. A method according to claim 1, wherein the collagen-containing membrane is delivered into a host organism or used in vitro.

4. A method according to claim 1, wherein the host organism is a human or animal.

5. A method according to claim 1, wherein the coating covers at least a portion of said collagen-containing membrane.

6. A method according to claim 1, wherein the coating further comprises natural or synthetic polymer, metal, metal oxide, oxide, metal nitride, borate, ceramic, zirconia, allograft hard tissue, allograft soft tissue, xenograft hard tissue, xenograft soft tissue, carbon nanostructure, carbon, glasses, natural or biocompatible material.

7. A method according to claim 1, wherein the metal nanoparticles have a size range from about 0.5 nm to about 500 nm.

8. A method according to claim 1, wherein the coating is capable of performing at least one of treating infection; preventing infection; treating inflammation; preventing inflammation; promoting cell adhesion; preventing biofilm formation; inhibiting biofilm formation; promoting cell proliferation; promoting binding with a biological or non-biological system; increasing or decreasing a cell function; delivering a drug and/or bioactive agent, or ensuring a better integration of a material into the host tissue.

9. A method according to claim 1, wherein the coating comprises one or more layers of metal nanoparticles.

10. A method according to claim 9, wherein the one or more layers comprises silver nanoparticles.

11. A method according to claim 1, wherein the medical device is an orthopaedic implant, dental implant, veterinary prosthetic device, a scaffold or a tissue engineering matrix.

12. A method according to claim 11, wherein the orthopaedic implant is a hip implant, knee implant or shoulder implant.

13. A method according to claim 11, wherein the dental implant is an abutment.

14. A method for inhibiting biofilm formation on a medical implant, comprising the step of covering said implant with a collagen-containing membrane that has been coated with silver nanoparticles so as to prevent biofilm formation and/or growth of bacteria, wherein said collagen-containing membrane is coated by sonication in a sonication bath to cause the metal nanoparticles to deposit and adhere onto a surface of the collagen-containing membrane.

15. A method according to claim 14, wherein the biofilm is a bacterial, a fungal, or a protozoan biofilm.

16. A method according to claim 14, wherein the medical implant is an orthopaedic or a dental implant, a scaffold or a tissue engineering matrix.

17. A method for inhibiting microbial colonization on a medical device or implant, comprising covering said device or implant with a collagen-containing membrane that has been coated with silver nanoparticles so as to prevent microbial colonization, wherein said collagen-containing membrane is coated by sonication in a sonication bath to cause the metal nanoparticles to deposit and adhere onto a surface of the collagen-containing membrane.

* * * * *